(12) United States Patent
Li et al.

(10) Patent No.: US 6,712,809 B2
(45) Date of Patent: Mar. 30, 2004

(54) EYE POSITIONING SYSTEM AND METHOD

(75) Inventors: Haizhang Li, Orlando, FL (US); Phuoc Khanh Nguyen, Winter Springs, FL (US)

(73) Assignee: Alcon RefractiveHorizons, Inc., Fort Worth, TX (US)

( * ) Notice: Subject to any disclaimer, the term of this patent is extended or adjusted under 35 U.S.C. 154(b) by 0 days.

(21) Appl. No.: 10/097,639

(22) Filed: Mar. 14, 2002

(65) Prior Publication Data

US 2003/0114841 A1 Jun. 19, 2003

Related U.S. Application Data

(63) Continuation-in-part of application No. 10/020,589, filed on Dec. 14, 2001.

(51) Int. Cl.[7] .............................................. A61B 18/18
(52) U.S. Cl. ............................... 606/4; 128/898; 606/5
(58) Field of Search ............................. 351/208; 606/4, 606/5

(56) References Cited

U.S. PATENT DOCUMENTS

| | | | |
|---|---|---|---|
| 5,463,430 A | | 10/1995 | Isogai et al. |
| 5,474,548 A | * | 12/1995 | Knopp et al. .................. 606/4 |
| 5,549,599 A | | 8/1996 | Sumiya |
| 5,562,656 A | * | 10/1996 | Sumiya .......................... 606/4 |
| 5,587,748 A | * | 12/1996 | Luce et al. ................. 351/208 |
| 5,620,436 A | | 4/1997 | Lang et al. |
| 5,634,920 A | | 6/1997 | Hohla |
| 5,645,550 A | | 7/1997 | Hohla |
| 5,909,268 A | * | 6/1999 | Isogai et al. ................ 351/208 |
| 6,004,313 A | | 12/1999 | Shimmick et al. |
| 6,030,376 A | | 2/2000 | Arashima et al. |
| 6,030,398 A | | 2/2000 | Klopotek |
| 6,217,570 B1 | * | 4/2001 | Nevyas ........................... 606/5 |
| 6,257,722 B1 | * | 7/2001 | Toh ............................. 351/208 |
| 6,280,436 B1 | * | 8/2001 | Freeman et al. ............... 606/5 |
| 6,322,216 B1 | * | 11/2001 | Yee et al. ....................... 606/5 |
| 6,361,168 B1 | * | 3/2002 | Fujieda ........................ 351/208 |

* cited by examiner

Primary Examiner—Roy D. Gibson
Assistant Examiner—Henry M. Johnson
(74) Attorney, Agent, or Firm—Allen, Dyer, Doppelt, Milbrath & Gilchrist, P.A.

(57) ABSTRACT

A system for positioning an eye for laser surgery includes a first and a second radiation generator positioned, respectively, to emit a first line and a second line orthogonal to the first line, the line generators positioned in a predetermined relation to a laser surgical system. A position of the eye is adjustable along an axis that is substantially perpendicular to the lines to achieve a positioning wherein the lines form a cross. The location of the cross is a preferred position for the eye relative to the laser surgical system for the laser surgery. Another embodiment comprises a first and a second spot generator positioned to project a first and a second spot onto an eye adjacent the clear cornea, between the clear cornea and the scleral rim. The eye position is adjustable for achieving a positioning wherein the spots are substantially vertically aligned.

5 Claims, 7 Drawing Sheets

EYE POSITIONING SYSTEM AND METHOD

CROSS-REFERENCE TO RELATED APPLICATION

This application is a continuation-in-part of and incorporates by reference co-pending application Ser. No. 10/020,589, filed Dec. 14, 2001, for "Eye Positioning System and Method," which is commonly owned with the present invention and which is incorporated herein by reference.

FIELD OF INVENTION

The present invention generally relates to objective measurements and surgical correction of a human eye and, in particular, to systems and methods for ensuring a correct positioning of the eye for surgery.

BACKGROUND

Laser surgery on the eye using laser in situ keratomileusis (LASIK) and laser epithelial keratomileusis (LASEK) is a common type of laservision correction procedure. It has proven to be an extremely effective outpatient procedure for a wide range of vision corrective prescriptions. The use of an excimer laser allows for a high degree of precision and predictability in shaping the cornea of the eye. Prior to the LASIK procedure, measurements of the eye are made to determine the amount of corneal material to be removed from various locations on the corneal surface so that the excimer laser can be calibrated and guided for providing the corrective prescription previously determined by measurement.

Procedures such as LASIK require precise alignment between the eye and the corrective laser beam. At present the patient is requested to focus on a fixation target such as a light-emitting diode (LED), but holding the eye steady during surgery may prove difficult.

It is also known to cross narrow beams at the apex of a curved surface, for example, at the top of a cornea. If the apex of the curved surface is substantially transmissive and/or specularly reflective, the intersection of the crossed beams at the apex is difficult to discern. Further, radiation safety is of concern in applications wherein the beams are permitted to remain impinging on the surface. In addition, in applications involving several dielectric interfaces such as in the eye, multiple reflections are likely to occur, which may create confusion in observation.

Thus there is a need to provide an accurate, safe, readily discernible reference for orienting the eye for surgery.

SUMMARY OF INVENTION

It is therefore an object of the present invention to provide a system and method for positioning an eye for surgery.

It is a further object to provide such a system and method that are substantially noninvasive.

It is an additional object to provide such a system and method that have less potential for harming eye tissue.

It is another object to provide such a system and method that provide a continuous indication of alignment.

These and other objects are achieved by the present invention, a first aspect of which includes a system for positioning an eye for laser surgery. The system comprises a first and a second line generator positioned, respectively, to emit a first line and a second line orthogonal to the first line. The first and the second line generators are further positioned in a predetermined relation to a laser surgical system.

Means for adjusting a position of the eye are positioned along an axis that is substantially perpendicular to the first and the second line. This location is for achieving a positioning wherein the first and the second line form a cross. The location of the cross comprises a preferred position for the eye relative to the laser surgical system for the laser surgery.

The method of the present invention comprises the steps of generating a first and a second line of radiation, wherein the first line is substantially orthogonal to the second line. The first and the second lines are directed to a position having a predetermined relation to a laser surgical system. A position of an eye is then adjusted along an axis substantially perpendicular to the first and the second line to achieve a positioning wherein the first and the second line form a cross on a cornea of the eye in a plane. This plane comprises a preferred position of the eye relative to the laser surgical system for laser surgery.

In an alternate embodiment, the patient bed can remain stationary, and the surgical system translated to the desired position as determined by the system of the present invention.

In another embodiment, a system for relatively positioning an eye and a surgical system for laser surgery comprises a first and a second radiation generator positioned, respectively, to emit a first beam and a second beam. Optics means are provided for focusing the first and the second beam into a first and a second spot, respectively, on a predetermined location of an eye. The optics means are positioned in a predetermined relation to a laser surgical system.

Means are also provided for adjusting a relative position of the first and the second radiation generators, the optics means, and the eye to achieve a preferred position for laser surgery, with reference to the locations of the first and the second spot. Thus the locations of the first and the second spot on the eye and relative to each other may be used as an indicator for achieving the preferred position for laser surgery.

The features that characterize the invention, both as to organization and method of operation, together with further objects and advantages thereof, will be better understood from the following description used in conjunction with the accompanying drawing. It is to be expressly understood that the drawing is for the purpose of illustration and description and is not intended as a definition of the limits of the invention. These and other objects attained, and advantages offered, by the present invention will become more fully apparent as the description that now follows is read in conjunction with the accompanying drawing.

DETAILED DESCRIPTION OF THE PREFERRED EMBODIMENT

Figure 1:
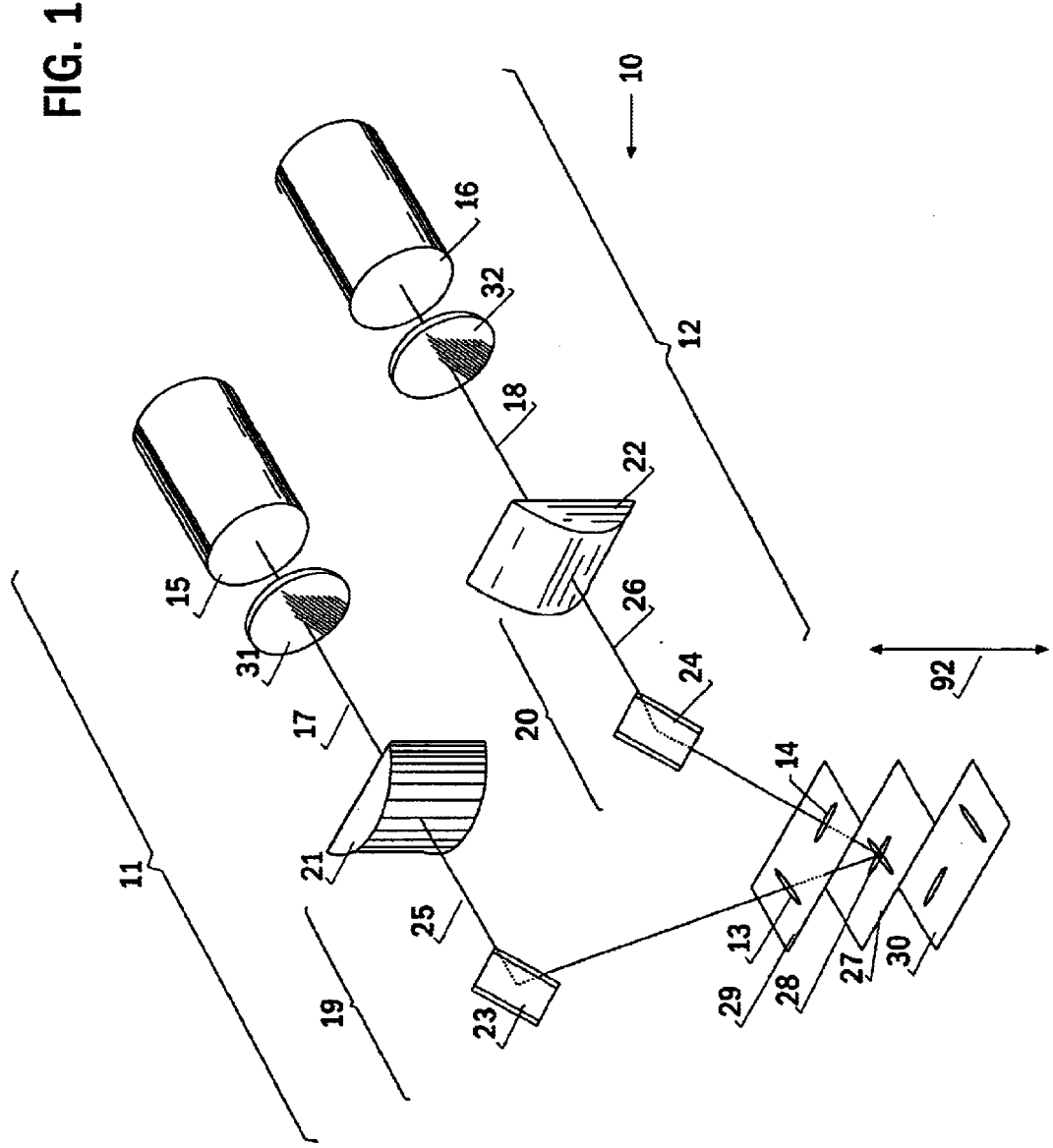
FIG. 1 is a schematic illustration of the optical system of a first embodiment of the present invention.
Figure 2:
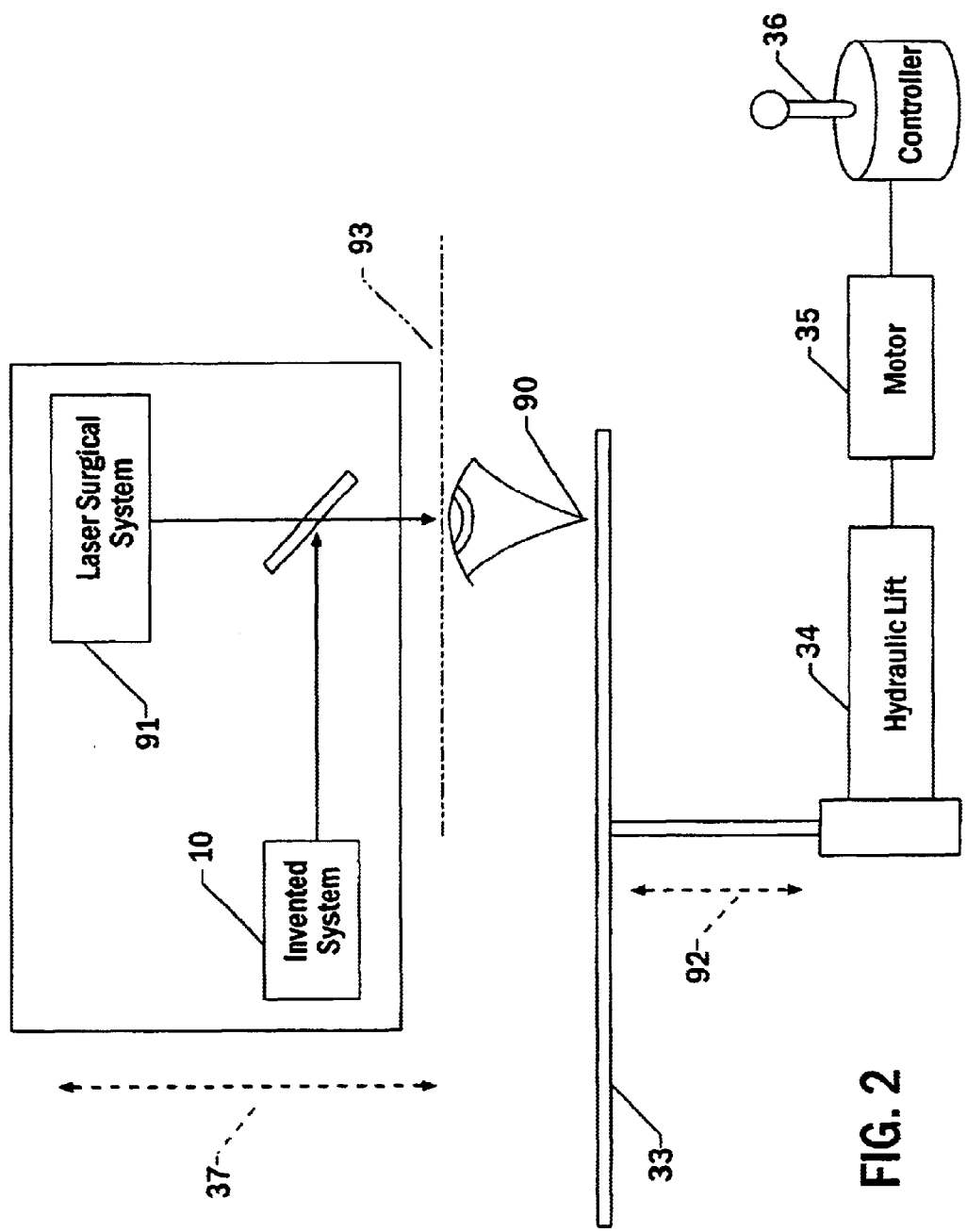
FIG. 2 is a schematic illustration of the surgical system incorporating the optical system of FIG. 1.
Figure 3:
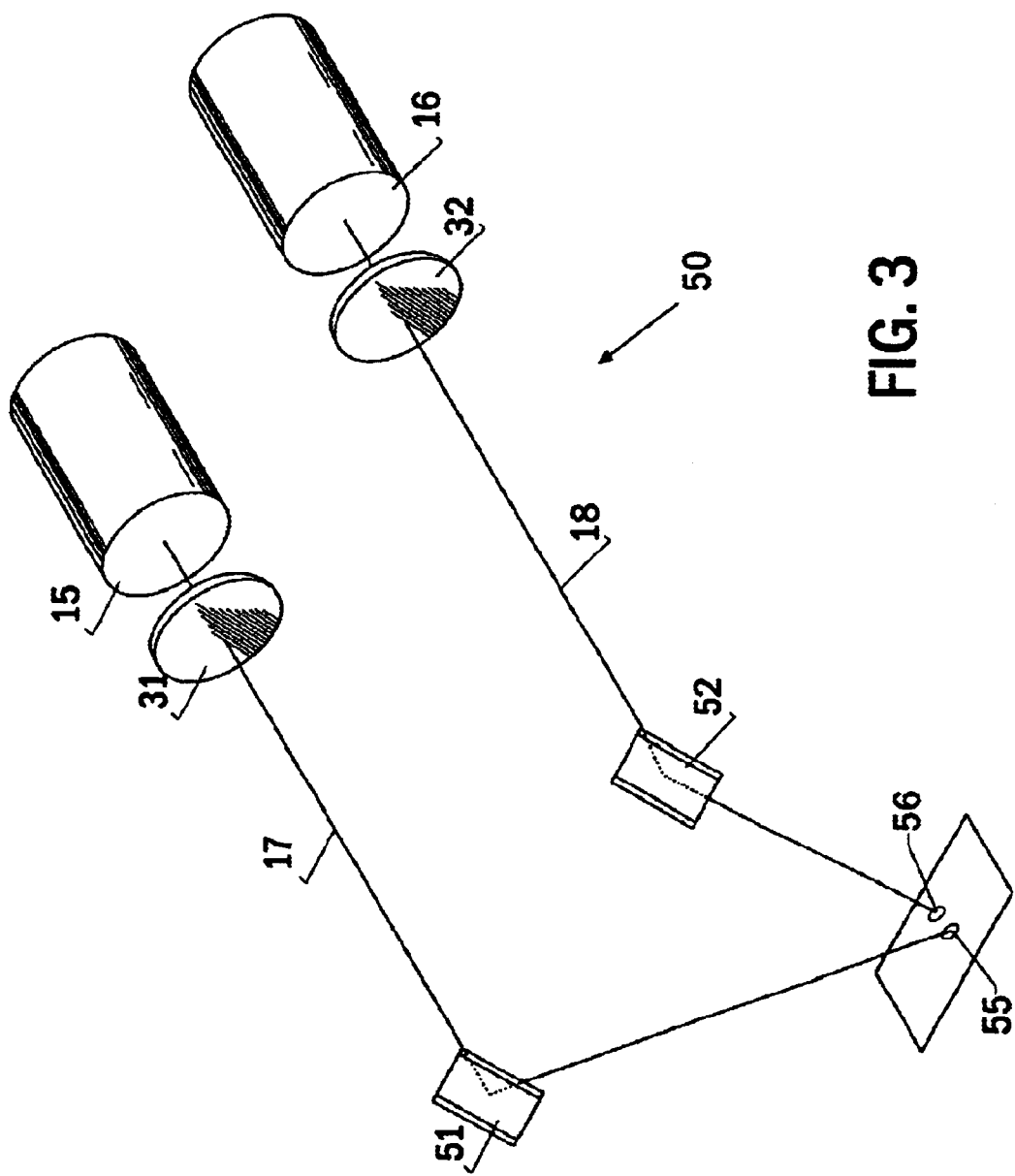
FIG. 3 is a schematic diagram of the optics for forming the first and the second spot.

A description of the preferred embodiments of the present invention will now be presented with reference to FIGS. 1–6B.

The system 10 of the present invention is for positioning an eye 90 for laser surgery, such as, but not intended to be limited to, LASIK surgery. The system 10 comprises (FIGS. 1 and 2) a first 11 and a second 12 line generator that are positioned, respectively, to emit a first line 13 and a second line 14 that is orthogonal to the first line 13. The first 11 and the second 12 line generator are further positioned in a predetermined relation to a laser surgical system 91.

In a preferred embodiment the line generators 11,12 comprise a first 15 and a second 16 source, for example, helium-neon (He—Ne) laser modules, for forming a first 17 and a second 18 beam of radiation. A first 19 and second 20 optical train transforms the first 17 and the second 18 beam into the first 13 and the second 14 line. The first 19 and the second 20 optical trains comprise in a preferred embodiment a first 21 and a second 22 cylindrical lens downstream of the first 15 and the second 16 laser source. The optical trains 19,20 further comprise a first 23 and a second 24 mirror downstream of the first 21 and the second 22 cylindrical lens, respectively. The first 23 and the second 24 mirror are oriented for-forming the lines 13,14 from the beams 25,26 emerging from the first 21 and the second 22 cylindrical lens. A preferred position 27 is indicated wherein a cross 28 is formed between the lines 13,14; positions above 29 and below 30 the preferred position are shown, wherein the lines 13,14 are disjoint.

The optical trains 19,20 additionally comprise a first 31 and a second 32 filter positioned between the first 15 and the second 16 laser source and the first 21 and the second 22 cylindrical lens.

Another aspect of the system (FIG. 2) comprises means for adjusting a relative position of the eye 90 along an axis 92 that is substantially perpendicular to the first 13 and the second 14 line. The adjusting means are for achieving the positioning wherein the first 13 and the second 14 line form the cross 28, which comprises a preferred position for the eye 90 relative to the laser surgical system 91 for laser surgery. In particular, the cross 28 is desired to be formed at a corneal eye plane 93 at which surgery is to be performed. If the lines 13,14 do not form a cross 28, then the eye position is not correct, which is indicated by the lines' 13,14 being disjunct in FIG. 1 at positions 29 or 30.

In a preferred embodiment of this embodiment of the present invention, the adjusting means comprises a patient bed 33 that is in mechanical contact with a means for moving the bed 33 along a substantially vertical axis 92. The moving means comprises, for example, a hydraulic lift 34, a motor 35 in activating contact with the lift 34, and a controller 36, such as a joystick or other implement known in the art, for controlling the motor 35.

Alternatively, the patient bed 33 can remain stationary, and the surgical system 91 translated as shown by the dotted double-headed arrow 37 to the desired position 27 as determined by the system 10 of the present invention.

In another, preferred embodiment of the invention (FIGS. 3–6B), the system 50 preferably comprises first 15 and second 16 laser modules with focusing lenses for generating two narrow, visible-wavelength laser beams 17,18. The beams 17,18 pass through filters 31,32, as above for system 10, and are directed via mirrors 51,52 to form spots 55,56 on the eye 90.

Figure 4:
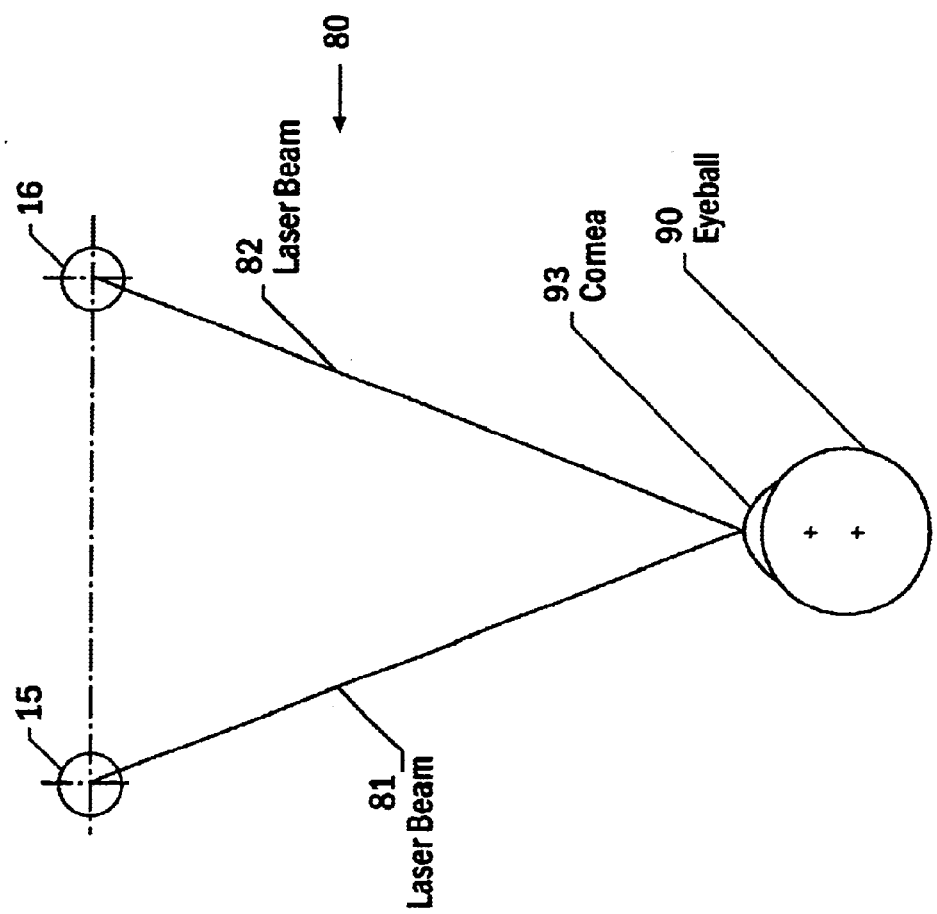
FIG. 4 (prior art) is a schematic diagram of laser beams crossing at the corneal apex.
Figure 5:
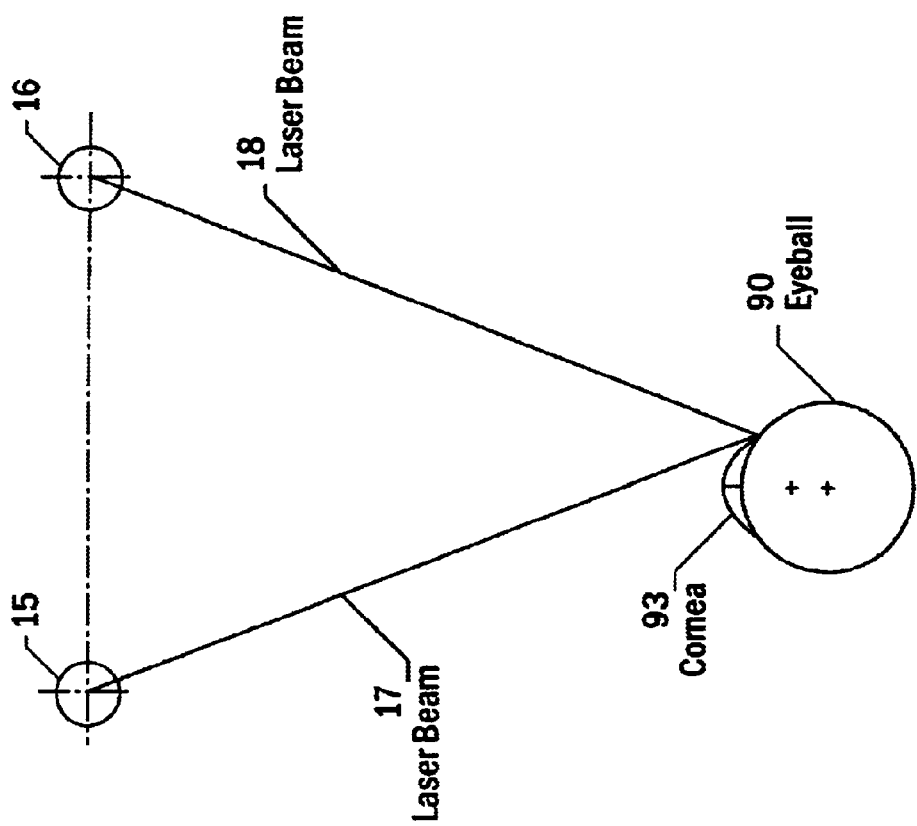
FIG. 5 is a schematic diagram of laser beams forming the first and the second spot adjacent the clear cornea.
Figure 6A:
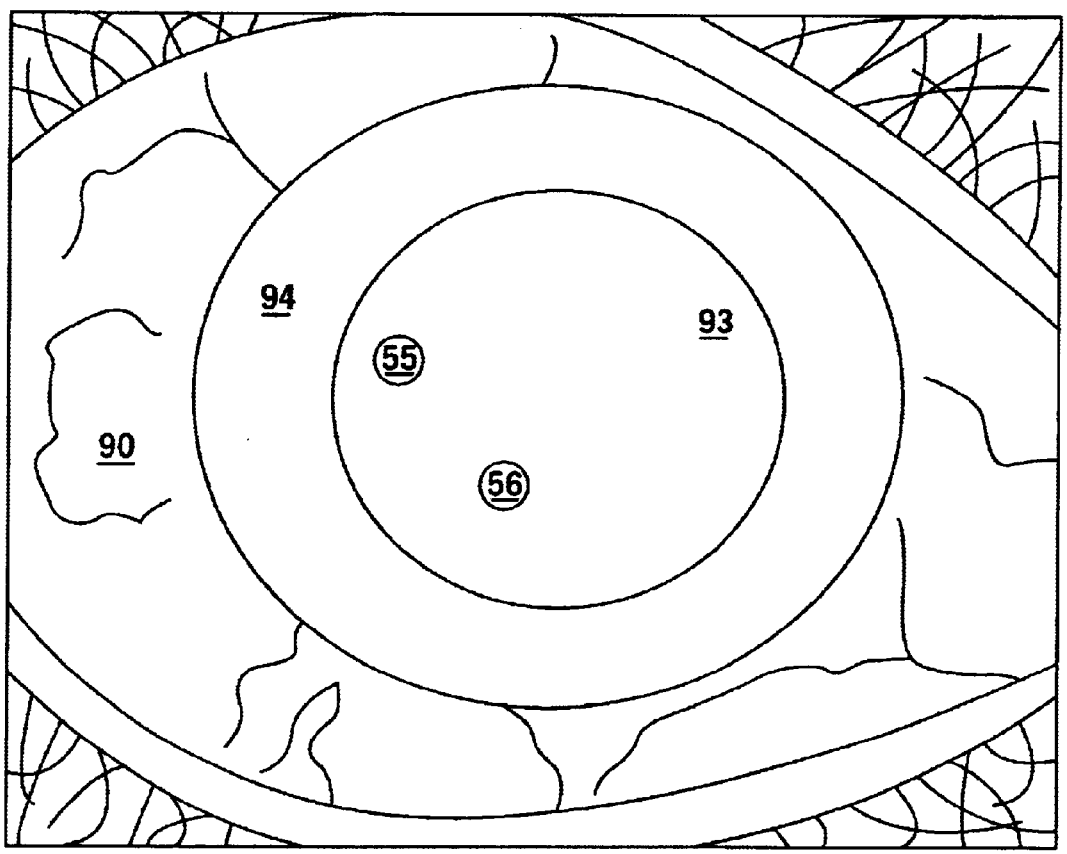
FIGS. 6A,6B illustrate improper (FIG. 6A) and proper (FIG. 6B) height alignment for performing surgery.
Figure 6B:
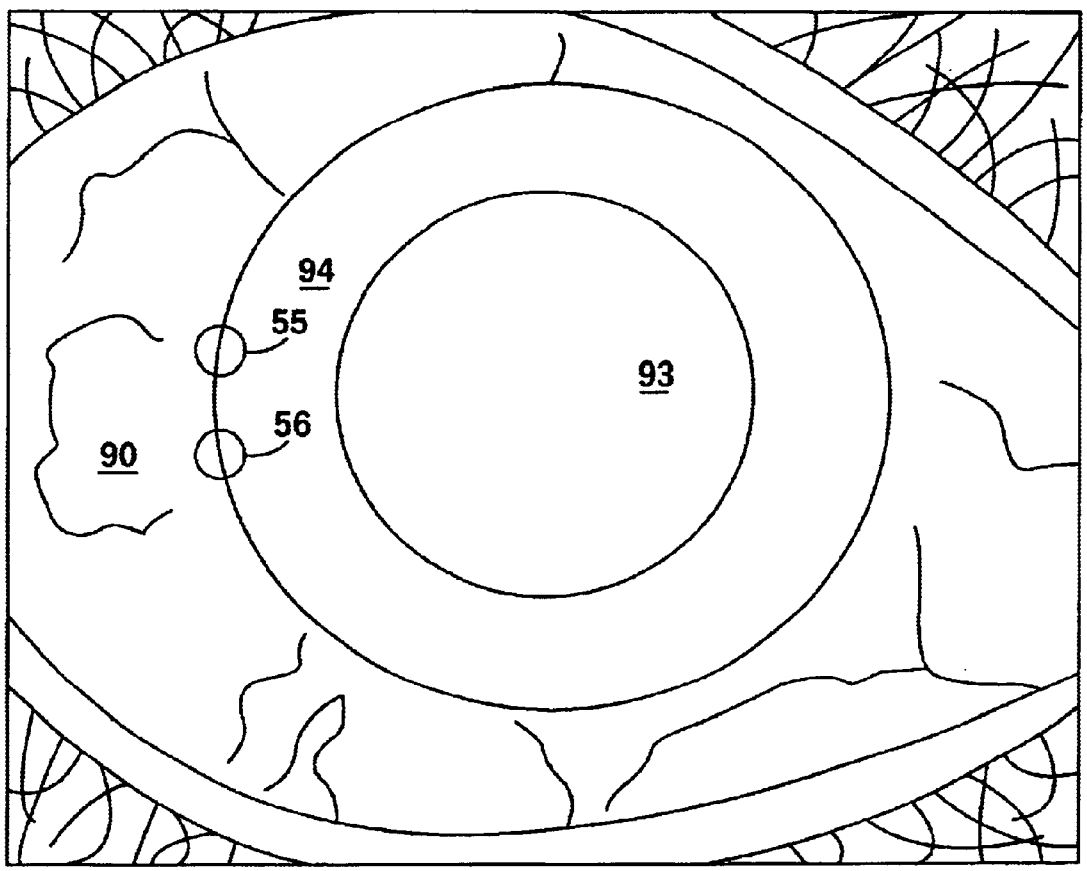

This embodiment 50 addresses a problem with prior art systems, such as that 80 shown in FIG. 4, wherein two narrow beams 81,82 cross at the apex of a curved surface, such as the top of the cornea 93, which, as discussed above, is transmissive and/or specularly reflective, making the discernment of crossed beams difficult, and also placing the beams 81,82 for long periods of time on the cornea apex.

In this embodiment of the present invention 50, preferably the beams 17,18 form spots 55,56 on an eye 90 adjacent the clear cornea 93, between the clear cornea and the scleral rim, which is the white tissue adjacent the clear cornea. Preferably the spots 55,56 should fall within ±1 mm of this boundary. When the eye 90 is in improper alignment (FIG. 6A), indicating that the bed 33 is not at a preferred height, the spots 55,56 fall on the eye 90 at a non-preferred location, here shown as on the cornea 93, skewed from verticality. If the bed 33 is moved upward, the lower spot 56 moves to the left and the upper spot 55 moves to the right in the orientation shown. If the bed 33 is moved downward, the lower spot 56 moves to the right and the lower spot 56 moves to the left. When the eye 90 is properly aligned (FIG. 6B), the spots 55,56 fall adjacent the clear cornea generally at the boundary with the scleral rim 94 in substantially vertical alignment, at a desired spacing, here, ±~1 mm.

Means for moving the eye 90 relative to the laser surgical system 91 are provided as above, wherein the eye position may be adjusted along an axis 92 perpendicular to a corneal plane 93 of the eye 90.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the apparatus illustrated and described herein are byway of example, and the scope of the invention is not limited to the exact details of construction.

Having now described the invention, the construction, the operation and use of preferred embodiments thereof, and the advantageous new and useful results obtained thereby, the new and useful constructions, and reasonable mechanical equivalents thereof obvious to those skilled in the art, are set forth in the appended claims.

What is claimed is:

1. A method for positioning an eye for laser surgery comprising the steps of:
    generating a first and a second beam of radiation;
    forming a first and a second spot from the first and the second beam, respectively;
    focusing the first and the second spots to a location adjacent a clear cornea on an eye having a predetermined relation to a laser surgical system;
    imaging the first and the second spots on the eye; and
    adjusting a relative position of the laser surgical system and the eye with reference to the first and the second spots imaged on the eye to achieve a preferred position for laser surgery.

2. The method recited in claim 1, wherein the first and the second beam generating step comprises forming a first and a second beam of visible-wavelength laser radiation.

3. The method recited in claim 1, wherein the adjusting step comprises moving a patient bed along a substantially vertical axis.

4. The method recited in claim 3, wherein the moving step comprises controlling a lifting means to move the patient bed.

5. The method recited in claim 1, wherein the adjusting step comprises moving the laser surgical system relative to a patient bed.

* * * * *